United States Patent [19]

Ter-Pogossian

[11] 4,150,292

[45] Apr. 17, 1979

[54] IMAGING DEVICE FOR COMPUTERIZED EMISSION TOMOGRAPHY

[76] Inventor: Michel M. Ter-Pogossian, 2 Brentmore Park, St. Louis, Mo. 63105

[21] Appl. No.: 770,108

[22] Filed: Feb. 18, 1977

[51] Int. Cl.² .............................................. G01T 1/20
[52] U.S. Cl. ............................ 250/363 S; 250/445 T
[58] Field of Search ................ 250/363 R, 363 S, 366, 250/369, 445 T

[56] References Cited
U.S. PATENT DOCUMENTS

| | | | |
|---|---|---|---|
| 3,329,814 | 7/1967 | Anger | 250/363 S X |
| 3,714,429 | 1/1973 | McFee et al. | 250/363 S |
| 3,970,853 | 7/1976 | Kuhl et al. | 250/363 S |

Primary Examiner—Davis L. Willis
Attorney, Agent, or Firm—Peter L. Berger

[57] ABSTRACT

A nuclear medicine imaging device is disclosed which provides tomographic sectional images of the human body subsequent to the administration of radio pharmaceuticals labelled with positron-emitting radionuclides. Signals representative of the distribution of the radionuclide within the patient are generated and are used in computerized tomography to reconstruct the region under examination. Elongated scintillation detectors are utilized to span a plurality of tomographic sections and positioning circuitry is utilized with the detectors for said tomographic sections. As an alternative embodiment, said detectors are arrayed coplanarly around the subject and generate suitable information for said computerized emission tomographic reconstruction.

31 Claims, 12 Drawing Figures

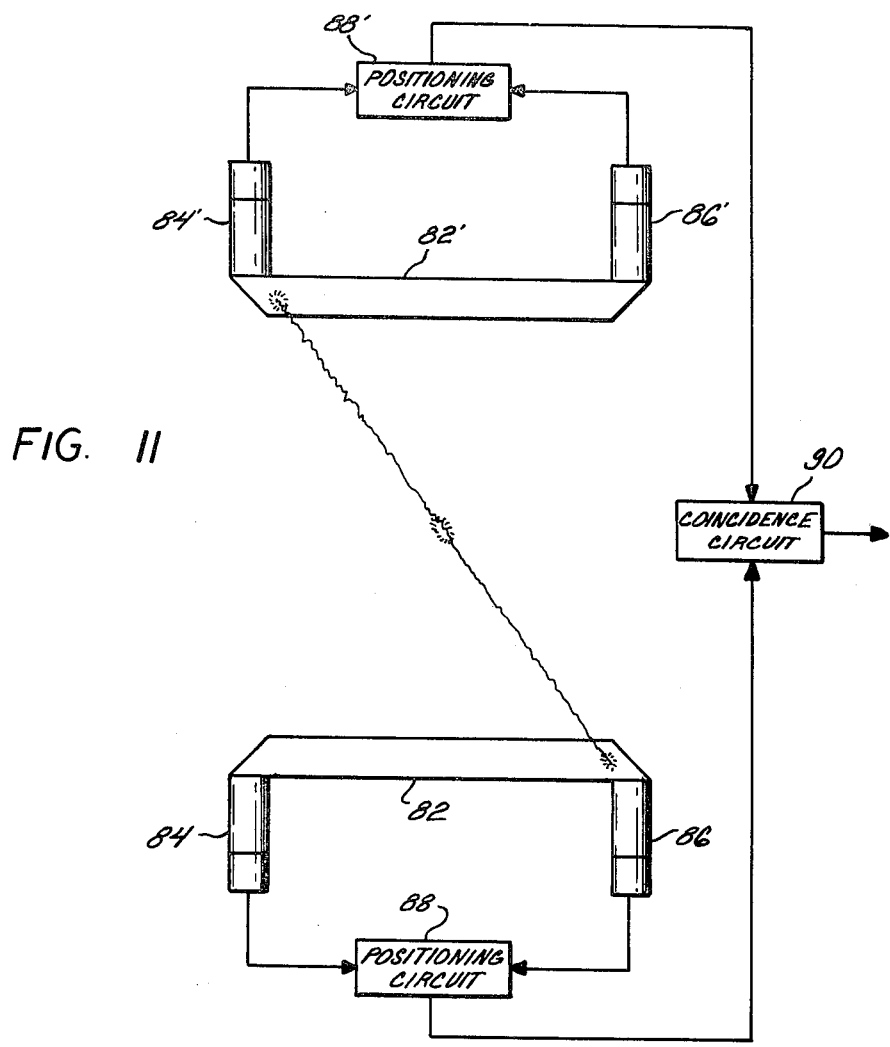
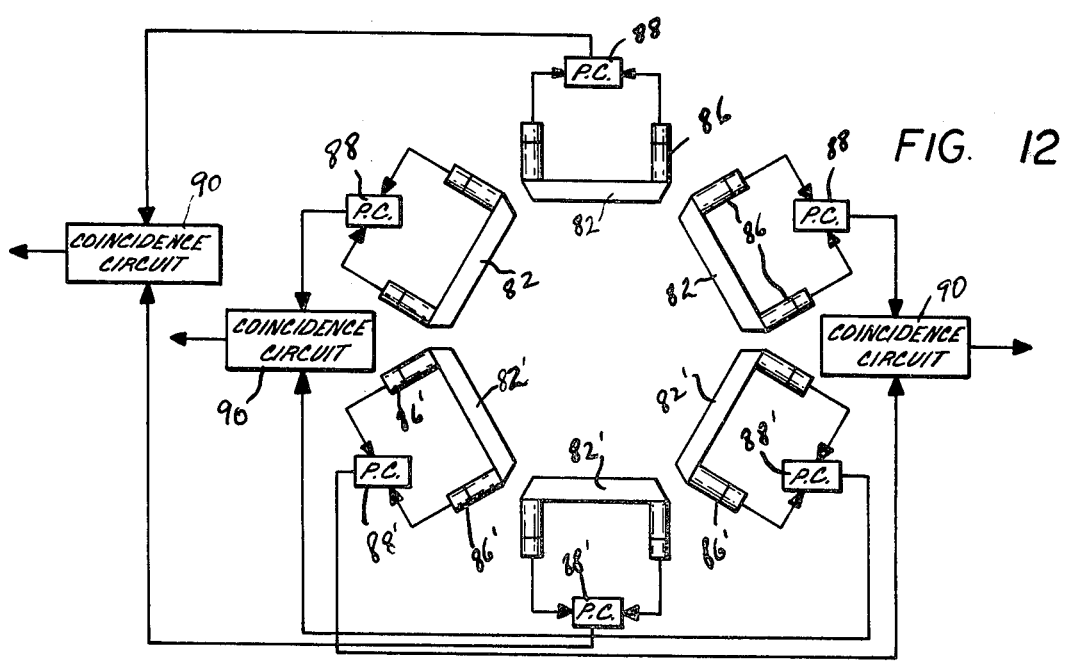

IMAGING DEVICE FOR COMPUTERIZED EMISSION TOMOGRAPHY

INTRODUCTION

This invention relates to an imaging device for nuclear medicine, and more particularly, to an imaging device which provides a reconstruction of an area under examination by forming tomographic sectional images of the human body under examination subsequent to the administration of radio pharmaceuticals.

The following references and material should provide the reader a more complete understanding of the environment of the present invention. The problems sought to be remedied by the present invention will be highlighted further on in this patent application, as will become more clear. To facilitate an understanding of the invention, computed axial tomography can be analogized to taking a series of "salami slices" through a patient under examination and utilizing the contents of the slices for image construction.

REFERENCES

1. Hounsfield, G., Ambrose, J., Perry, J., Bridges, C. Computerized transverse axial scanning. Brit, J. Radiol 46:1016, 1973.
2. Ter-Pogossian, M. M., Phelps, M. E., Hoffman, E. J., Eichling, J. O. The extraction of the yet unused wealth of information in diagnostic radiology. Radiol 113:515, 1974.
3. Cho, Z. H. General views on 3-D image reconstruction and computerized transverse axial tomography, IEEE Trans Nucl Sci NS-21, No. 3:44, 1974.
4. Brooks, R. A., G. Di Chiro, Principles of computer assisted tomography (CAT) in radiographic and radioisotopic imaging. Review article. Phys Med Biol 21:689–732, 1976.
5. Shepp, L. A., Logan, B. F., The Fourier reconstruction of a head section. IEEE Trans Nucl Sci NS-21:21, 1974.
6. Freedman, G. S., editor. Tomographic Imaging in Nuclear Medicine, New York, Society of Nuclear Medicine, 1973.
7. Kuhl, D. E., Edwards, R. Q., Ricci, A. R., Reivich, M. Quantitative section scanning. In Medical Radioisotope Scintigraphy, Vol. 1, IAEA, Vienna 1973, pp 347–353.
8. Kuhl, D. E., Hale, J., Eaton, W. L. Transmission scanning: A useful adjunct to conventional emission scanning for accurately keying isotope deposition to radiographic anatomy. Radiol 87:278–284, 1966.
9. Bowley, A. R., Taylor, C. G., Causer, D. A., Barger, D. C., Keyes, W. I., Undrill, P. E., Corfield, J. R., and Mallard, J. R. A radioisotope scanner for rectilinear, arc, transverse section and longitudinal section scanning; (ASS - the Aberdeen Section Scanner). Brit J. Radiol 46:262–271, 1973.
10. Patton, J. A., Brill, A. B., King, P. H. Transverse section brain scanning with a multicrystal cylindrical imaging device. In Tomographic Imaging in Nuclear Medicine, G. S. Freedman, editor, New York Society of Nuclear Medicine, 1973, pp.
11. Tanaka, E. Multi-crystal section imaging device and its data processing. Proc XIII Int Conb Radiol Madrid, 15–20 Oct. 1972.
12. Kuhl, D. E., Edwards, R. Q., The Mark IV system for emission computerized tomography and quantitative reconstruction of brain radioactivity. J. Nucl Med 16:543, 1975 (abstract).
13. Kay, D. B., Keyes, J. W., Simon, W. Radionuclide tomographic image reconstructions using Fourier transform techniques. J Nucl Med 15:981–986, 1974.
14. Budinger, T. F., Gullberg, G. T. Three-dimensional reconstruction of isotope distributions. Phys Med Biol 19:387–389, 1974.
15. Chesler, D. A. Positron tomography and three-dimensional reconstruction technique. In Tomographic Imaging in Nuclear Medicine, G. S. Freedman, editor, Society of Nuclear Medicine, New York, 1973, pp 176–183.
16. Muehllehner, G. Section imaging by computer calculation. J. Nucl Med 12:76–84, 1971.
17. Cormack, A. M. Reconstruction of densities from their projections, with application in radiological physics. Phys Med Biol 18:195–207, 1973.
18. Keyes, W. I. A practical approach to transverse-section gamma-ray imaging. Brit J Radiol 49:62–70, 1976.
19. Chesler, D. A. Three-dimensional activity distribution from multiple positron scintigraphs (abstract). J. Nucl Med 12:347–348, 1971.
20. Robertson, J. S., Marr, R. B., Rosenblum, M. et al. 32 Crystal positron transverse section detector. In Tomographic Imaging in Nuclear Medicine, G. S. Freedman, editor, Society of Nuclear Medicine, New York, 1973, pp 142–153.
21. Ter-Pogossian, M. M., Phelps. M. E., Hoffman, E. J., Mullani, N. A., A positron-emission transaxial tomograph for nuclear imaging (PETT). Radiol 114:89–98, 1975.
22. Phelps, M. E., Hoffman, E. J., Mullani, N. A., Ter-Pogossian, M. M. Application of annihilation coincidence detection to transaxial reconstruction tomography. J. Nucl Med 16:210–224, 1975.
23. Cho, Z. J., Eriksson, L., Chan, J. A circular ring transverse axial positron camera. In Reconstructive Tomography in Diagnostic Radiology and Nuclear Medicine, M. M. Ter-Pogossian, editor, University Park Press, Baltimore, in press.
24. Derenzo, S. E., Zaklad, H., Budinger, T. F., Analytical study of a high-resolution positron ring detector system for transaxial reconstruction tomography. J. Nucl Med 16:1166–1173, 1975.
25. Lim, C. B., Chu, D., Kaufman, L. et al. Initial characterization of a multiwire proportional chamber positron camera. IEEE Trans Nucl Sci 22:388–394, 1975.
26. Brownell, G. L., Burnham, C. A., Hoop, B., Jr., Kazemi, H. Positron scintigraphy with short-lived cyclotron produced radiopharmaceuticals. In Medical Radioisotope Scintigraphy, Vol. 1, IAEA, Vienna, 1973, pp. 313–330.
27. Hoffman, E. J., Phelps, M. E., Ter-Pogossian, M. M., Mullani, N. A., Higgins, C. S.: Design and performance characteristics of a whole body positron transaxial tomograph. J. Nucl Med 17-493-502, 1976.

In this patent application the terms computerized and computed are used interchangeably, such as computerized tomography or computed tomograph (CT).

BACKGROUND OF THE INVENTION

Tomography, both transaxial and longitudinal, has been used in diagnostic radiology for some time. The term transmission computed (axial) tomograph (CT refers to a diagnostic radiologic procedure which provides images of transverse sections of the body. CT permits accurate and non-invasive quantitative determination of the x-ray absorption properties of anatomical structure buried deeply in the human body or of the distribution of a radionuclide or of photon emission events in the body.

Generally in diagnostic positron emission CT, a patient is administered a radionuclide, causing millions of positrons to be emitted within the patient. These positrons travel for very short distances, no more than a few millimeters, and in their travel interact with electrons of similar mass. When the positrons and electrons interact, there is an annihilation which takes place and the annihilation event which occurs consists of the mass of the positron and electron being annihilated or disintegrated, with photons being emitted substantially at 180 degrees with respect to each other. The photons then travel the distance required to impinge upon detectors. In the detectors, the energy carried by the annihilation photons is converted to a flash of light, and it is this flash of light which is sensed by photomultiplier tubes located at the ends of the detectors which is a recording of the annihilation which took place within the subject.

In the space of a few minutes, hundreds of thousands of such "flashes of light" will be generated and electrical signals representing these flashes are processed by a system which may include a specially programmed digital computer so as to form an image of the area under examination. In the emission CT process of this invention only those annihilation photons travelling within certain planes (or slices), are counted in such reconstruction.

In computerized tomographic reconstruction, measurements are taken of the radiation intensity along each of a great number of straight paths which are all in the same plane, and this same plane is what defines the planar, tomographic section or slice. If this slice is considered to be divided into a two-dimensional matrix of slice elements by an imaginary grid, then each of those elements is intersected by a number of the paths. The measurements include one for each of these paths, and they can be processed in accordance with the techniques disclosed, for example, in U.S. Pat. Nos. 3,778,614 and 3,924,129 to form a map of a radiation-related characteristic of these slice elements. If X-ray radiation propagates along these paths, the characteristic is typically the X-ray absorption of each slice element. If the radiation is gamma photons or annihilation photons, the characteristic is the number of such photons emitted due to events occurring in the slice element (per unit time).

When this invention is practiced, the detectors of photons and the determinations of the paths of the detected photons are used to determine the number of such photons (per unit time) detected along each of these paths. The paths can have an arbitrarily selected width (their thickness or the thickness of the slice being imaged). A typical width in my invention may be of the order of mm, or at most up to a few cm. A typical thickness may be of the same order.

For determining the radiation intensity, a beam of radiation is produced and is collimated to a pencil beam or to a planar fan beam. This beam passes through the patient and, after further collimation, impinges upon a scintillation detector consisting of at least one luminescent crystal optically coupled to a photomultiplier tube. This tube provides electrical signals corresponding to the amount of radiation impinging on the crystal. The X-ray tube and the detector are connected rigidly. They scan the object to be examined in a linear translational motion called a transverse. After one such transverse, the gantry supporting the source and the detector steps rotationally (e.g., 1 degree) about an axis perpendicular to the section to be imaged, and another transverse occurs. Typically, this operation is repeated to cover a total of at least 180 degrees. The measurements of radiation made by this technique can be considered as a series of profiles of the attenuation of X-rays in the matter traversed at different angles. It is from these profiles that the image of the anatomy of the tomographic section is reconstructed. Any difference in X-ray attenuation to be reconstructed in the image must appear in the profiles.

The radiation transmission profiles which are acquired by the CT detector system are recorded in a digital form. From this, the CT system generates the image of the section. A number of different techniques have been used in tomographic reconstruction, such as those disclosed in said U.S. Pat., Nos. 3,778,614 and 3,924,129.

The reconstruction technique to be used in my invention is known as the "filtered back projection" reconstruction technique detailed in U.S. Pat. Nos. 3,924,129 and 3,778,614 and in the above references 4 and 5. The radiation detectors often used for this purpose are scintillation crystals, e.g., activated sodium iodide crystals coupled to photomultipliers or photodiodes, although xenon detectors and other crystals have also been used.

A number of radionuclides decay through the emission of positrons. One physical characteristic of these particles is highly serendipitous for the CT imaging of the radionuclides which emit them.

Positrons are positively charged electrons usually emitted by radionuclides which are unstable because they include an excess of neutrons with respect to a stable state. Positrons lose their kinetic energy in matter in a manner similar to that of electrons. However, as briefly described above, when positrons are brought to rest they undergo the phenomenon of annihilation, whereby the positron interacts with an electron, the two particles undergo annihilation, and the masses are converted into energy in the form of two photons called the annihilation photons. These two photons travel at about 180 degrees from each other and each carries an energy of approximately 511 keV. It is through the simultaneous detection of the two annihilation photons that positron-emitting radionuclides are of significance in CT reconstruction.

The annihilation radiation can be uniquely detected by two scintillation detectors connected to a coincidence circuit. In this scheme, a count is recorded only if both detectors detect the annihilation photons simultaneously. This method of detection provides an "electronic" collimator since the annihilation events occurring outside a straight line joining the two detectors cannot be recorded (except in a statistically insignificant occurrence) because the annihilation photons are emitted at about 180 degrees from each other. Thus, two detectors operated in coincidence establish a field of view encompassed by the lines joining them.

The advantages of positron emission CT have been recognized, (see references 17 and 19-24), and several systems have been designed and tested. The overwhelming majority of these designs incorporate scintillation or imaging detectors. Hereinafter, the term detector shall be used to describe any detector useful in nuclear medicine imaging techniques. In its simplest form, a positron emission CT system consists of two detectors facing each other and scanning across the object at different angles. In order to achieve high efficiency in collecting the radiation, more detectors can be placed around the object. Another design for this purpose consists of a circle of detectors rotating around the object to be imaged.

It should be noted that the diagnostic tomographic visualization of an organ typically requires several tomographic sections. Thus, tomographs capable of yielding only one section at a time must be operated sequentially with relative motion of the tomograph with respect to the patient between sections. This approach is wasteful of radiation, time consuming, and often unsuitable for the study of time-dependent dynamic phemonena throughout the organs images. Furthermore, the accurate indexing of the apparatus with respect to the patient is difficult. To alleviate this difficulty state-of-the-art positron imaging systems incorporate the ability to provide several sections simultaneously. Thus, the MGH positron camera does provide a number of simultaneous CT sections (see reference 26).

SPECIFIC BACKGROUND PROBLEMS SOUGHT TO BE REMEDIED BY THE INSTANT INVENTION

As discussed above, the present invention is primarily directed to positron emission transaxial tomographic nuclear image systems, an example of which is specifically disclosed and illustrated in references Nos. 21 and 27 (See FIG. 1), above. The problem identified above of a single section being analyzed at a time was present, and one approach which could be used to avoid that problem is identified above in reference No. 27. In this approach, large detectors plates are placed on opposite sides of a patient. Disadvantages of this approach include the large number of detectors employed, the missing of radiation information emitted in directions outside the area covered by the plates, and the time consuming nature of this procedure, among other problems.

Another possible approach to simultaneously generate a plurality of tomographic sections (salami slices) is to provide pluralities of banks of detectors, one on top of the other. As seen in FIG. 1, a plurality of detectors is arrayed around the subject under examination, and these detectors are arrayed in a single plane. The subject is generally extending transversally to said plane and along the longitudinal axis. As a consequence of using banks of said detectors, simultaneous three dimensional measurements may be effected. One of the problems with such an arrangement is that there are a large number of such detectors required. For instance, in the specific illustration set forth in FIG. 1 above, there are 48 detectors used for each plane, and with four simultaneous planes being generated, there would be 192 of said detectors. Additionally, the physical constraints regarding the construction and operation of these detectors requires that there be translational movement along both the longitudinal and transaxial axes in order to cover those portions of the subject under examination which is unable to be examined and lies between the geometrical physical constraints of the detectors.

It should also be noted that even with the single section (slices) formed by the plurality of detectors surrounding the subject as in FIG. 1, 48 such detectors are required. Additionally, translational movement is required in order to obtain counts between the centers of the detectors, since the geometry of the apparatus causes blank spaces to be formed between adjacent detectors. Moreover, care must be taken to maintain all of those detectors calibrated relative to each other and relatively free of the effects of drift and other nonlinearities.

A specific object of my invention is to be able to generate images of a plurality of tomographic sections (salami slices) simultaneously so as to provide simultaneous three dimensional information without the attendant large number of individual detectors required in the prior art.

Another object of my invention is to provide an arrangement for detecting the distribution of a radionuclide within a patient for tomographic computerized analysis which substantially eliminates many of the large numbers of detectors rquired in the prior art.

Still another object of my invention is to provide a relatively inexpensive, yet effective apparatus for providing a tomographic section analyzing the distribution of radionuclides within a patient under examination.

Other objects, advantages and features of my invention will become more apparent from the following description.

BRIEF DESCRIPTION OF THE DRAWINGS

FIG. 11 is an end view showing yet another embodiment of my imaging device invention employing elongated detector tubes to form a single tomographic plane or section to be examined.

FIG. 12 is an end view similar to FIG. 11 of another embodiment of my invention.

DETAILED DESCRIPTION OF THE INVENTION

Figure 1:
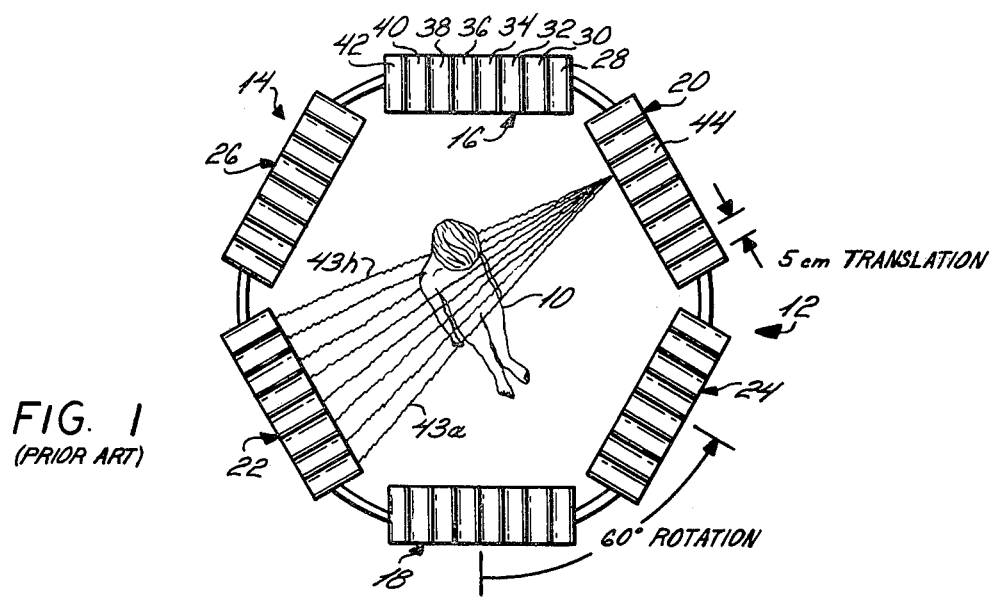
FIG. 1 is an end perspective view of a prior art imaging device for performing sectional computerized positron emission tomographic analysis.

The above description regarding the background and environment of this imaging device invention should help the reader understand my specific improvement and advance in the art. In furtherance of that understanding, reference is made to FIG. 1 which is an end perspective view of a prior art computerized positron emission transaxial tomographic imaging device employing a plurality of detectors forming a plane for examination. In particular, the subject 10 under examination is shown extending through the ring, plane, or section 12 formed by a plurality of sets of detectors 14, arranged around the subject. The sets of detectors 14 are arranged in three pairs, with each one of the pair being located opposite the other, as indicated by pairs 16 and 18, 20 and 22, 24 and 26. Each group of detectors itself comprises a plurality of adjoining detectors as at 28–42 of detector set 16. The ends of the detectors are arranged to face the subject, and all the detectors lie in the same plane, thus forming a transaxial section or slice having a thickness defined by the large size of the detector ends.

When a positron emitting radionuclide is administered to a subject, a number of positrons is emitted within the patient, as described above. These positrons react with electrons within the subject, and upon the annihilation of the positron and electron, oppositely directed annihilation photons traveling about 180 degrees with respect to each other are emitted. These photons may be sensed in pairs of opposite detectors surrounding the patient and give rise to the tomographic analysis employed herein.

Relating the above description to the specific showing of FIG. 1, there is shown a plurality of individual lines 43a–43h extending through the patient from one individual detector 44 located within detector set 20 to the plurality of detectors. As may be understood, the annhiliation photons can be emitted from the patient in any plane or direction, and, accordingly, only those photons emitted in the same plane are used for tomographic analysis. Thus, if photons are detected or sensed as received in the opposite detector sets simultaneously, it may be presumed that the photons were emitted simultaneously from the same annihilation event within the subject. Thus, as commonly employed for positron analysis, a coincidence detector is employed in combination with the opposite sets of detectors to count only those detected events which are sensed simultaneously in oppositely located sets of detector tubes. As described above, in the space of a few minutes there are hundreds of thousands of annihilation events occurring and sensed within the plane under examination, although there are many, many more such events which occur and produce oppositely moving photons which do not move exclusively within the tomographic plane or section under examination. In this manner, a tomographic section or "salami slice" is made through the patient, examining the radionuclide distribution in the patient by computerized emission tomography, in which the sensed events which are detected in oppositely located detector sets are combined to produce a map of the radionuclide density distribution in that section of the patient under examination.

The device illustrated in FIG. 1 is one of the more advanced for such examination, but has several disadvantages. In particular, because the detectors have fixed geometrical constraints, there is a significant distance between adjacent centers, so that during the examination process, the sets of detectors must be translated, that is, moved parallel to each other in opposite directions in increments which are small enough to allow for measurements between the adjacent locations of the detector tubes. Further, because the detectors do not completely encircle the patient, rotation of the detectors is employed to move one detector set, such as 14, to the position of the adjacent set, such as at 20, which comprises a 60 degree rotation. Such a rotation is accomplished in small increments, and with such small incremental rotational steps as well as the incremental translational steps, a complete tomographic section or slice is formed with the imaging device apparatus of FIG. 1.

As stated in the above description, only a single such transaxial section or "salami slice" is capable of being imaged at any one time with the apparatus illustrated in FIG. 1. This is problematic, since the subject to be examined extends in all three dimensions, and in order to examine multiple slices, the apparatus illustrated in FIG. 1 must be duplicated to simultaneously generate a number of such sections, or in the alternative, the patient be incrementally longitudinally moved with respect to the apparatus. Each of these alternatives presents significant problems, with the first alternative of providing duplicate sets of such detector sets coaxially arranged not being very practical because of the large number of such detectors required, and their size. The expense of producing such a scanner, where, for instance, four simultaneous sections are to be examined is very high. Further, the complexity of dealing with such a large number of such detector tubes including the associated electronic and mechanical apparatus is also problematic. As a further problem, it can be seen that the problem relating to the distance between adjacent centers of such detectors as illustrated above in a single plane would also be present with a multiple sectional tomographic device in which the ring illustrated in FIG. 1 is reproduced in the third or longitudinal dimension to produce simultaneous sectional analysis. Therefore, such a device would have to have translation in a circular direction as well as translation in the longitudinal direction. This presents unique problems which would severely impair the ability to produce a workable and useable three dimensional tomographic sectional analytical scanner employing identical sets of the single section imaging device of FIG. 1.

The alternative of using the single ring illustrated in FIG. 1, and moving the patient through that ring, is also disadvantageous because of the resultant degradation of the quality of the image through motion artificats, which are either physiological, such as heartbeat, blood vessel pulsations, respiration and peristalsis, or due to patient movement. Furthermore, there is a change in the radionuclide distribution with time because of blood or other flow in the body, and the natural migration of the radionuclide. Extended examination times are also burdensome to the patient, and encumber equipment which is expensive to operate. Further, since the administration of a radionuclide is not without constraints, it is always desirable to minimize levels of radiation to which a patient is subjected. The device illustrated in FIG. 1 is described in more detail in references Nos. 21 and 27.

Figure 2:
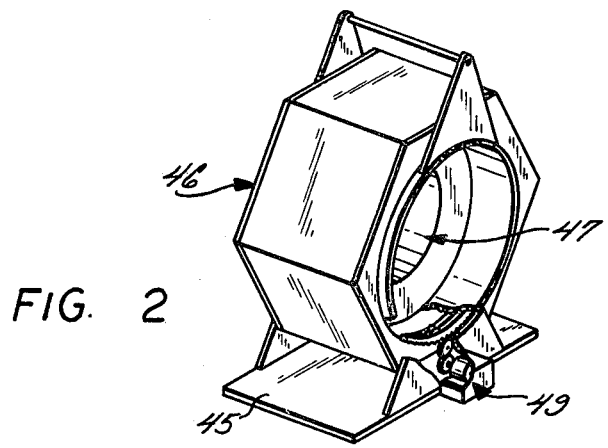
FIG. 2 is a side perspective view of an embodiment of my imaging device of this invention.

Referring now to FIG. 2, there is shown a perspective end view of one embodiment of my imaging device invention. There is shown a platform or base 45 upon which rests a drum or housing 46 of a generally hexagonal outer shape with an annular inner circular opening 47 through which a patient 10 extends. The housing has a depth generally extending in the direction of the patient and is defined substantially by the elongated dimension of the detector (See FIG. 3).

In the prior art device of FIG. 1, the ends of the detectors were facing the patient, and it should be noted that elongated dimension (FIG. 3) is much greater than the facing dimension of the end of the detector. Consequently, a larger area of the patient in the longitudinal (long) direction is subject to examination than that available in FIG. 1. This larger area extends in a direction substantially perpendicular to the tomographic transaxial sections formed through the patient 10, the detector serving to allow a plurality of tomographic sections simultaneously to be formed, as will be described in more detail hereinafter. The significance of this will be developed hereafter.

A motor and drive gear assembly 49 is provided to rotate the drum or housing 46 to measure points unavailable at any one setting because of the geometry separating adjacent centers.

Figure 3:
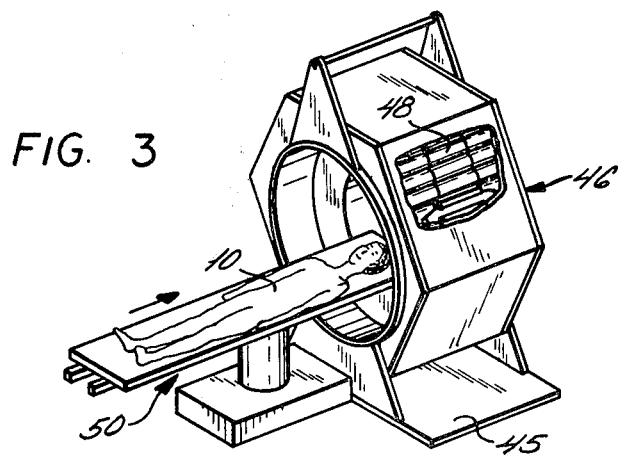
FIG. 3 is an end partial sectional perspective view of the imaging device of FIG. 2, showing a patient to be examined, in place.

Referring to FIG. 3, there is shown a partial broken away sectional perspective view of my imaging device of FIG. 2, with the patient 10 shown on a bed 50. The head and shoulder portion of the patient extends in the circular opening to permit three dimensional simultaneous tomographic data gathering by my imaging device. The embodiment shown in FIG. 3 employs sets of detector tubes around the patient, with the sets being formed by elongated tubes located next to each other. Other embodiments of my tomographic imaging device will be described below.

Figure 4:
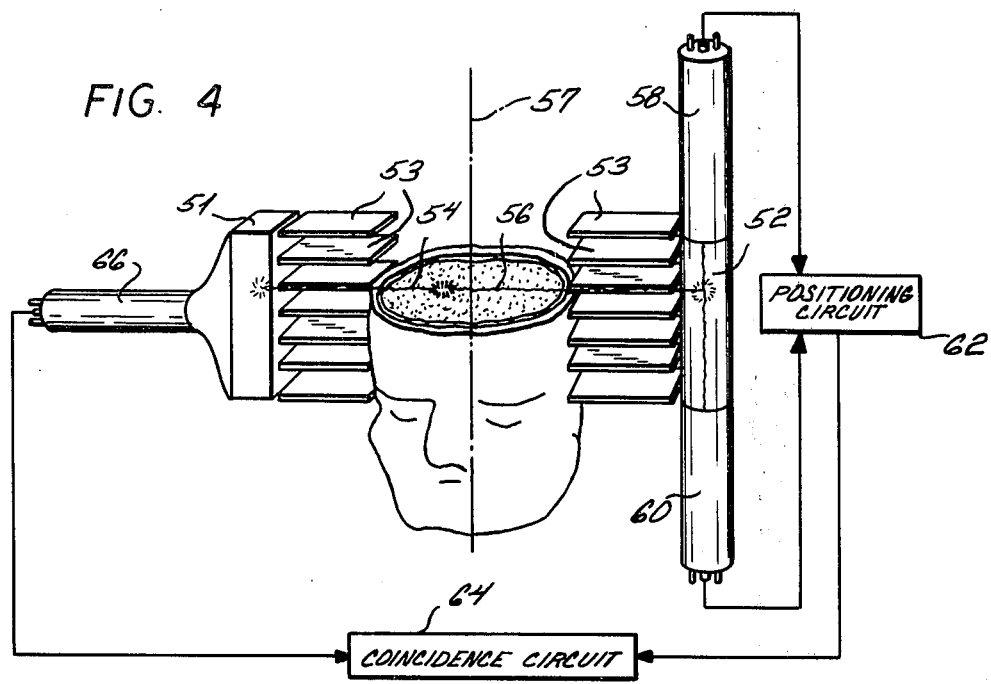
FIG. 4 is a partial perspective view of another embodiment of my invention illustrating one arrangement of detectors.

Referring to FIG. 4, there is shown a partial perspective block functional diagram of another embodiment of my invention. A plate detector 51 is located opposite from a scintillation detector tube 52, with the patient under examination located therebetween. It is to be understood that the illustration in FIG. 4 shows only a single elongated detector opposite the detector plate, but in practice, the elongated detectors would be formed in sets as appropriate opposite corresponding detector plates to surround the subject under examination. For purposes to be described hereinafter, there are also provided a plurality of spaced apart, parallel, transaxially oriented lead septa 53, which serve to sectionalize the view of the detector plate 51 and detector tube 52 into a plurality of transaxial tomographic sections to be set forth hereinafter.

A single annihilation event giving rise to oppositely directed annihilation photons 54 and 56 enables the photons to propagate in approximately opposite directions, as illustrated, at approximately the speed of light. When the photons are emitted in a tomographic transaxial plane or slice perpendicular to the long axis 57 through the patient, they can pass directly to the opposite detectors 51 and 52, while when the photons are not coplanar with that slice, they will be prevented from reaching the opposite detectors because of the lead septa 53. The end of each detector tube 52 is associated with oppositely located photo-multiplier tubes 58 and 60 connected to its ends so that when a scintillation event occurs in the detector 52, a flash of light results, which is sensed by the photomultiplier tubes 58 and 60.

The occurrence of an event in the detector tube is signaled through a positioning circuit 62 which is connected to one input of a conventional coincidence circuit 64. Each of the photomultipler tubes 58 and 60 converts the flash of light into an electrical signal and the positioning circuit utilizes the respective electrical signals generated to identify where along the length of the detector tube the scintillation event occurred. Such a position circuit is conventional in the art, and an example of such is found in U.S. Pat. No. 3,688,113 entitled Tomographic Radiation Sensitive Device issued on Aug. 29, 1972 to Fluro D. Miraldi. The output of detector plate 51 is connected to another photomultiplier tube 66, the output of which is connected to the other input of coincidence circuit 64. When the coincidence circuit registers that scintillation events occur simultaneously in both the detector plate 51 and detector tube 52, this is an indication that these events were most likely caused by photons from a single annihilation event oppositely traveling along a line being located in one of the tomographic sections defined by septa 53. The actual position of the location of the scintillation event along the length of detector tube 52 is also sensed and developed by position circuit 62 for process in the computerized reconstruction, and this will be explained in further detail hereinafter.

Referring now to FIGS. 1 and 4, it is seen that detector tube 52 essentially extends over a plurality of transaxial tomographic sections along the longitudinal or long axis perpendicular to the plane of the tomographic sections or "salami slices" formed. The position circuit 62 is for the purpose of ascertaining in which plane of the tomographic planes the scintillation effect was sensed, and this information is used as part of the reconstruction process. It is further to be noted that a single detector tube 52 in conjunction with a detector plate 51 is illustrated in FIG. 4. To reduce the need to rotate the detector plate 51 and detector tube 52 there could be a plurality of detector plates opposite corresponding sets of groups of elongated detector tubes.

Figure 5:
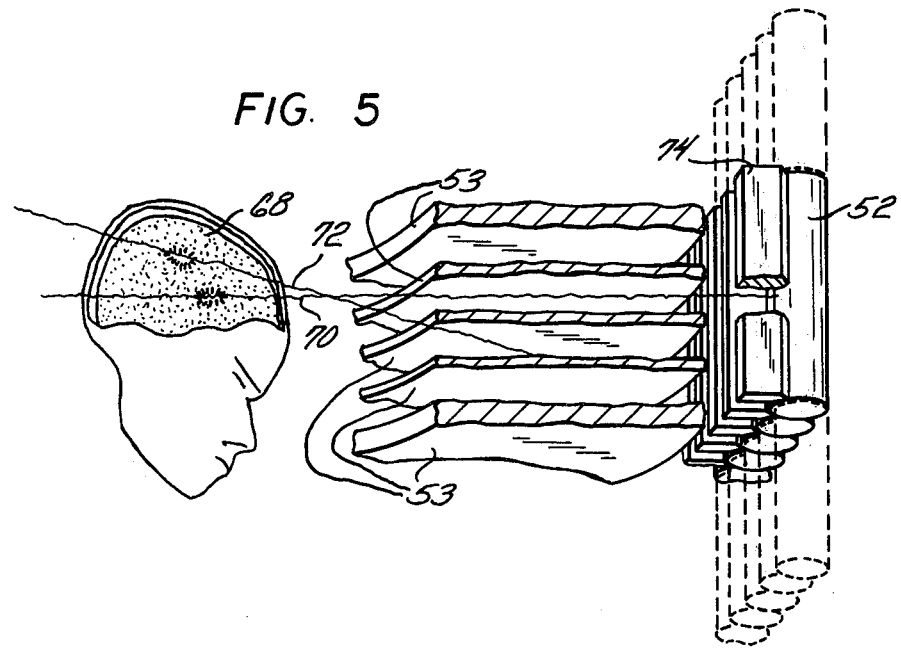
FIG. 5 is a perspective view of one set of detectors forming an embodiment of my invention, utilizing collimators and lead septa.
Figure 6:
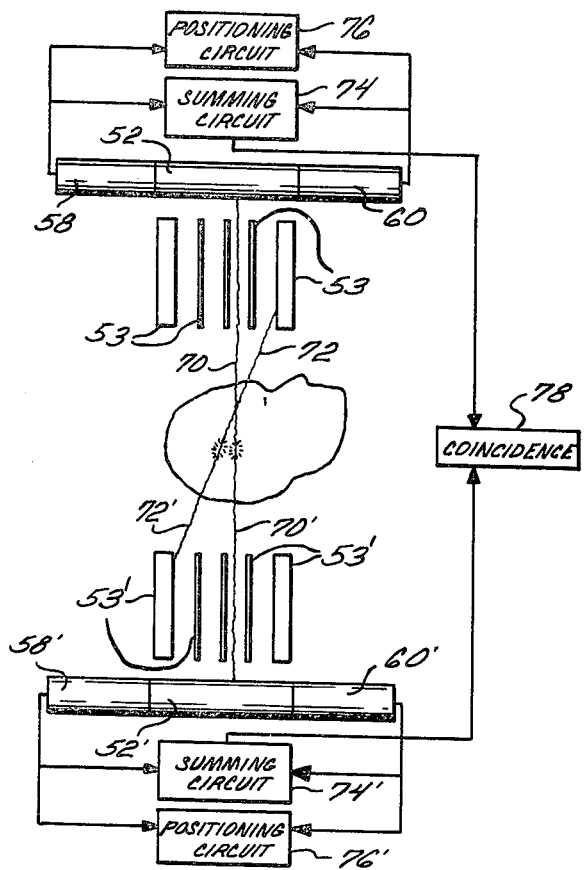
FIG. 6 is a functional block diagram illustrating the use of opposite elongated detectors which form another embodiment of my invention, with the arrangement of a plurality of said detectors shown in FIG. 5.

Reference is now made to FIGS. 5 and 6 which illustrate further aspects and embodiments of my invention. In FIG. 5, there is shown a perspective view of a section of a head 68 under examination, and the propagation of photons 70 and 72 caused by corresponding annihilation events. As can be seen, photon 72 will be absorbed by one of the parallel transaxial lead septa 52, while photon 70 will pass through to the detector 52. Lead collimators 74 are placed in front of and parallel to the lengths of detector tubes 52 to define channels in which the photons will travel and interact with the detector crystals, such that each corresponding photomultiplier tube can produce a non-ambivalent electrical signal. As illustrated in FIG. 5, a plurality of such elongated detector crystals 52 are arranged side by side with pairs of photomultiplier tubes being connected at opposite ends thereof. Due to the geometry of the lead septa there may be a large gap separating adjacent transaxial "salami slices" because of a "shadowing effect". Suitable translational movement of the entire assembly in a direction along the length of the detectors at least over a distance corresponding to at least the thickness of a septum, is employed. This translational movement will allow measuremeants to be made in the gaps between the channels formed by the septa.

In FIG. 6, there is shown a pair of oppositely located detector crystals 52 and 52' with detector crystal 52 replacing detector plate 51 of FIG. 4. A pair of photomultiplier tubes 58 and 60 are associated with detector crystal 52, while photomultipliers 58' and 60' are connected at opposite ends of detector crystal 52'. A plurality of septa 53 are located in front of detector 52', while septa 53' are located in front of detector 52'. As will be explained hereinafter, in the present invention, these septa may be unnecessary because of the use of the respective positioning circuits to form a "sectioning means", to be described hereinafter.

Assuming an annihilation event occurs somewhere in the subject under examination as a result of the administration of a radionuclide, a plurality of pairs of oppositely moving photons as in FIG. 5 will be generated along respective lines, those photons being labelled as 72, 72' and 70 and 70'. Since the line describing the movement of photons 72 and 72' extends beyond the thickness of a transaxial tomographic section formed for analysis, these will not be detected in detectors 52 and 52', and will be absorbed by septa 53 and 53' respectively. Photons 70 and 70' travel along a line lying within one of the tomographic sections formed for analysis, and these will be sensed by detectors 52 and 52', respectively. Upon detection, a flash of light is generated which is sensed in the respective photomultiplier tubes 58 and 60 and 58' and 60' located at the ends of detectors 52 and 52'. These flashes of light are converted to electrical signals and as described above with reference to FIG. 4 are supplied to respective summing circuits 74 and 74' and positioning circuits 76 and 76'. Thus, when summing circuits 74 and 74' indicate that a flash of light of a given intensity has been sensed within detectors 52 and 52', coincidence circuit 78 will generate such a signal.

The information developed in position circuits 76 and 76' is used to indicate the location along the detectors 52 and 52' at which the scintillation event was sensed. This information is also supplied in the computerized tomographic reconstruction process, which has been described above in this specification and in U.S. Pat. Nos. 3,778,614 and 3,924,129 and reference 5.

Figure 7:
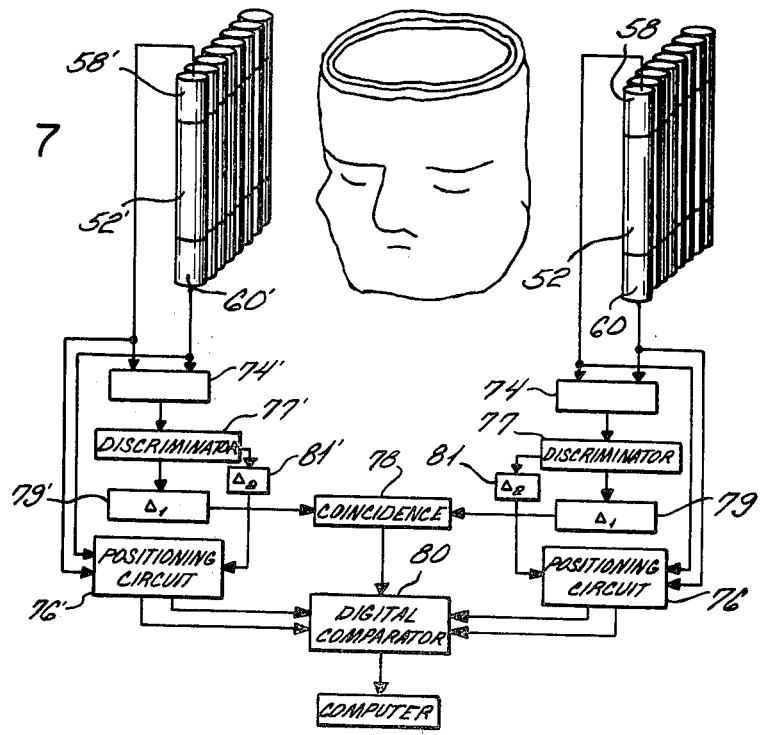
FIG. 7 is a more detailed functional block diagram illustrating a plurality of groups of detectors used without septa.

FIG. 7 illustrates yet another embodiment of my invention in which septa 53 and 53' in FIG. 6 are eliminated. In other respects the apparatus of FIG. 7 is similar to that of FIG. 6. The subject under examination is placed between the groups of detectors 52 and 52', which have respective photomultiplier tubes 58 and 60 and 58' and 60' connected at their respective ends. The outputs of the photomultiplier tubes are supplied to respective summing devices 74 and 74', it being understood that each pair of photomultiplier tubes has an associated summing device therewith. The electrical outputs of the summing devices 74 and 74' are supplied to pulse height discriminators 77 and 77' and then through respective delay lines 79 and 79' to coincidence circuit 78 which generates an output if an event is simultaneously detected in any of the sets of detector tubes 52 and 52'. The discriminators 77 and 77' are conventional and serve to reject those detected events which produce less than a predetermined amount of said flash of light. The summer and discriminator is a Le Croy Model 623Z.

Position circuits 76 and 76' also receive the outputs from photomultiplier tubes 58 and 60 and 58' and 60' and supply their respective outputs to a conventional digital comparator 80. Delay lines 81 and 81' are located between respective discriminators 77 and 77' and position circuits 76 and 76'. The position circuits generate digital representations which are compared bit by bit in comparator 80. It should be recognized that there will be a repeat of the electronics shown for each tube, as appropriate. The output of the digital comparator is then supplied to the computer for purposes of computerized reconstruction.

When the position circuits 76 and 76' indicate that the locations of the simultaneously received scintillation events occurred at substantially the same vertical positions, that is, within one of the transaxial sections, then data related to said detected even will be forwarded for processing along with the actual position detected. Thus, the position circuits 76 and 76' in combination, are able to section the longitudinally extending dimension of the detector 52 and 52' into a plurality of tomographic transaxial sections (salami slices), with the size of each section being limited to the electronics and geometry required to distinguish between adjacent spots on the detector where the events are detected. Therefore, the septa are not needed to form said sections. If simultaneously detected events detected in respective psoition circuits 76 and 76' are not sensed to lie within the same plane, then those detected events are not counted for purposes of tomographic reconsturction.

Delay lines 77, 77', 79 and 79' ensure that the coincidence determination 78 occurs before the position comparison 80 and enables the position comparison to proceed, if coincidence is present.

Recounting the imaging device of FIG. 1 in comparison with that of FIG. 7, it may be seen that my present imaging device provides the ability to simultaneously form multiple parallel transaxial sections for simultaneous generation of three dimensional data. This powerful tool allows a large portion of the patient to be examined simultaneously rather than section by section time sequence analysis.

Figure 8:
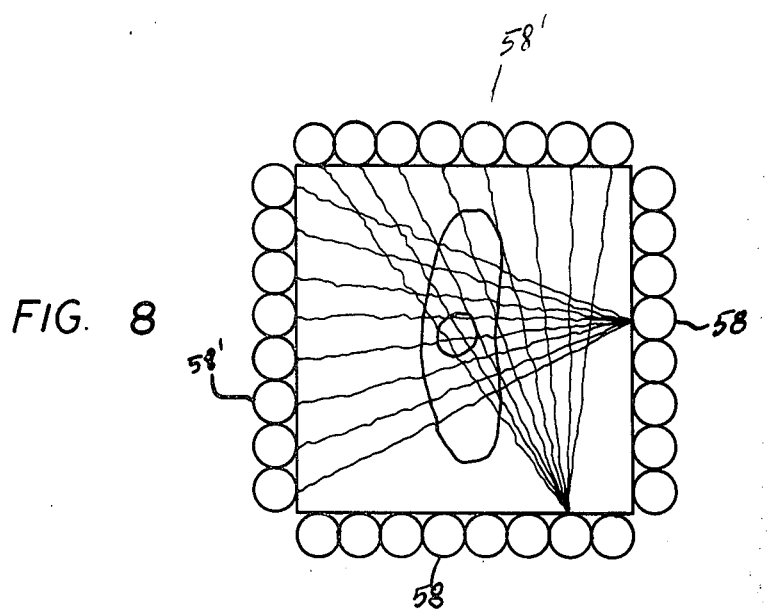
FIGS. 8–10 are end views illustrating different arrays for the detector tubes to surround the patient.
Figure 9:
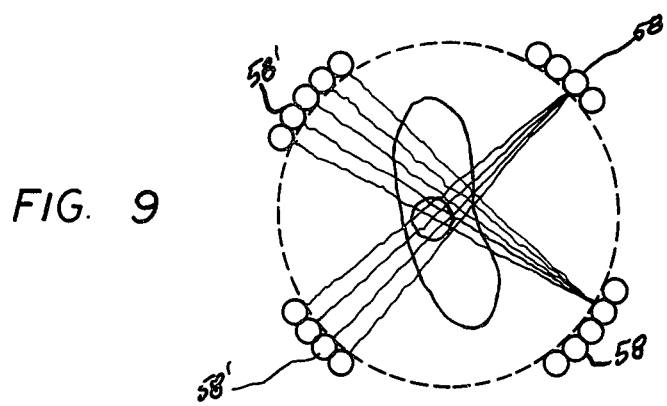
Figure 10:
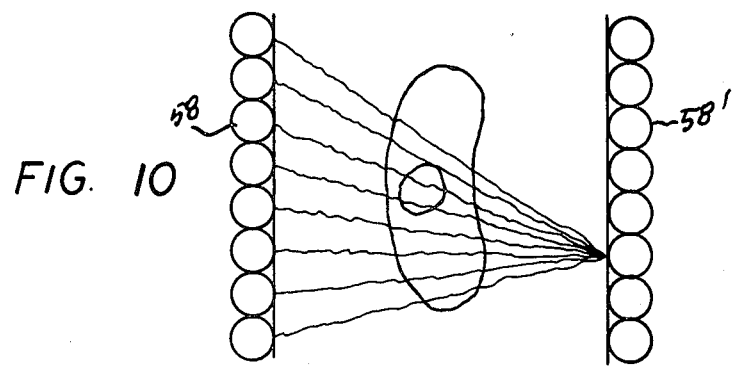

FIGS. 8–10 illustrate various other arrangements for the detectors capable of being employed around the patient for the axial tomography of my invention. FIG. 8 illustrates the detectors being located on four sides, FIG. 9 indicates the detectors as being adjacent to one another on a ring and FIG. 10 indicates the groups of detectors being formed on opposite sides. In each of these figures the detectors are elongated and their lengths are transverse to the planes of the tomographic slices and span two or more slices. The measurements are made by the detectors in all three dimensions simultaneously to develop a three dimensional matrix of the distribution of the radioactive material in the patient. The combination of this three dimensional material can be accomplished along any of the three axes for image reconstruction. Thus, the reconstruction can be transaxial as illustrated by U.S. Pat. Nos. 3,778,614 and 3,925,129, or longitudinal.

As can be appreciated, the longitudinal viewing face of the detectors is sectioned by the position circuit, and in combination with the coincidence circuit 78 and comparator 80 a sectioning means is formed for enabling a large number of events to be detected in the longitudinally extending viewing faces of the oppositely disposed detectors. In this fashion, a plurality of tomographic transaxial parallel sections is formed through the patient with measurements being produced and utilized in the computerized tomographic reconstruction process.

Referring to FIG. 1, in the prior art, there is seen that a single tomographic transaxial section is formed with six banks of detectors being arranged side by side. As yet another embodiment of my invention, and by referring to FIG. 11, I propose to replace six of these sets of detectors with oppositely extending parallel individual detectors 82 and 82', each having respective photomultiplier tubes 84 and 86 and 84' and 86' located at their respective ends, the detectors by their parallel relationship forming a plane under examination. The far ends of detectors 82 and 82' are cut at a bias and treated so as to provided reflective surfaces viewed by photomultiplier tubes. When events are sensed by detectors 82 and 82' simultaneously, it means that the annihilation event which occured in the patient generated photons moving along a line lying within a single tomographic sectional plane. As in FIG. 7, the outputs of the opposite photomultipliers 84–86 and 84'–86' are supplied to respective position circuits 88 and 88'. The outputs of position circuits 88 and 88' are supplied to coincidence circuit 90 to indicate whether or not the photons were detected simultaneously. The positions at which the detected events are sensed along the respective detectors 82 and 82', are generated by the position circuits 88 and 88', respectively, and are utilized in the tomographic reconstruction process.

In FIG. 11, only a pair of oppositely located parallel elongated detectors is illustrated for examining a patient, and this pair can be rotated in the same tomographic plane to different positions around the patient to provide a complete tomographic section. This is a relatively inexpensive alternative scheme to replace the opposite sets of individual detectors, such as those in groups 14 and 18 of FIG. 1, and yet have the added ability to give increased resolution as compared with the prior art imaging device. It is remembered that in the prior art device shown in FIG. 1, translational movement of the banks of individual detectors was required to obtain measurements in the gaps formed between centers of the adjacent detectors. In the embodiment of my invention illustrated in FIG. 11, such translational movement is unnecessary, since there are no gaps along the viewing face of the detector. Further, the resolution obtainable with these detectors 82 and 82' is significantly greater than that which could be obtained by the side by side detectors of FIG. 1.

With the embodiments of FIGS. 7 and 11 illustrating my invention, it can be seen that the detector facing area which views the scintillation even spans across the distance which at least two individual detectors occupied. Thus, reconsidering the embodiment of FIG. 1 it can be seen that the detector in FIG. 11 spans across the ends of several detectors and forms a plurality of "individual" detectors for tomographic transaxial sectional analysis, although only a pair of individual detectors is used. With regard to FIG. 7 the elongated detector spans several tomographic sections to replace the suggested multiple banks of detector sets of FIG. 1.

As yet another embodiment of my invention in FIG. 12, there is illustrated six individual detectors lying within the same plane surrounding the patient, with each of the detectors associated with a pair of photomultiplier tubes in the same manner as is FIG. 11. In this way, rotation of the detectors around a patient is minimized as compared with the embodiment shown in FIG. 11, and the translational movement required for the six banks of detectors in FIG. 1 is eliminated with the construction of FIG. 12 in comparison to that obtained with the apparatus of FIG. 1. It can also be understood that the six detectors and twelve photomultipliers replace the 48 detector tubes illustrated in FIG. 1.

Another embodiment of my invention which is not illustrated in the drawings but can be readily understood would allow the elongated detectors of FIGS. 11 or 12 which form a transaxial plane for measurement to be reproduced in the longitudinal direction. Thus banks of such a ring of detectors could be placed one on the other to obtain three dimensional measurements for forming a three dimensional matrix of the radioactive material in the patient. Translational movement of the layered detectors perpendicular to their long dimension would be desirable to obtain measurements in the gaps between adjacent detectors.

My invention may also find beneficial use with gamma emitting radionuclides administered to a patient.

Additionally, my invention is shown as being responsive to photon emission events within a patient receiving a dosage of radionuclide. It is understood that photon emission events within a patient are achievable by a source thereof outside a patient, such as by using a positron source. My imaging device can operate with emission events whether produced by internal radionuclides or an external source.

It should be understood that the above description of my invention illustrates several embodiments thereof. To one skilled in the art numerous obvious substitutions and changes can be made which would produce a system still practicing my invention.

What is claimed is:

1. An imaging device for computerized emission tomography wherein a patient is treated to cause the generation of photons within a three-dimensional region of the patient's body, said photons moving outwardly from within said region and exiting the patient, a planar tomographic section of the region being imaged to form a two-dimensional map of the distribution in the section of the generation of said photons, said imaging device comprising,
   a detector spanning the region along at least one of said dimensions and detecting the spatial distribution of said exiting photons along said dimension,
   position circuit means coupled with the detector to establish the positions along said dimension at which said photons are detected and
   means coupled with the detector and position circuit means to form back projection signals, and
   computerized planar tomographic reconstruction means for tomographically reconstructing said spatial distribution of said exiting photons.

2. An imaging device as set forth in claim 1, wherein said imaging device comprises at least a pair of said detectors located on opposite sides of the patient, respective position circuit means connected to each of said detectors, means for supporting said detectors to be within the same plane defined by said planar tomographic section, said one dimension of said three orthogonal dimensions lying within said plane of said planar section, and coincidence circuit means connected to said respective position circuits to identify which exiting photons are simultaneously detected in said pair of detectors.

3. An imaging device as set forth in claim 2, wherein each of said pair of detectors is of an elongated geometry, with the long dimension of said detectors being located in said planar section.

4. An imaging device as set forth in claim 3, wherein each of said pair of detectors is tubular in shape.

5. An imaging device as set forth in claim 1, wherein said imaging device comprises at least two pairs of said detectors located on opposite sides of the patient, respective position circuit means connected to each of said detectors, means for supporting said pair of detectors to be within the same plane and within said planar tomographic section, said one dimension of said three orthogonal dimensions lying within said planar section, and coincidence circuit means connected to each pair of position circuit means which are connected to opposite detectors, each of said coincidence circuit means identifying which exiting photons are simultaneously detected in opposite pairs of detectors.

6. An imaging device as set forth in claim 5, wherein each of said pairs of imaging detectors comprises an elongated shape, with the long dimension of said shape being located in said planar section.

7. An imaging device as set forth in claim 1, wherein the dimension in which said detector extends is perpendicular to said planar tomographic section, further comprising means to section said detector to form a plurality of parallel planar tomographic sections.

8. An imaging device for computerized emission tomography wherein a patient is treated to cause the generation of photons within a three-dimensional region of the patient's body, said photons moving outwardly from within said region and exiting the patient, a plurality of parallel aligned planar tomographic sections of the region being imaged to form a plurality of two-dimensional maps of the distribution in the sections of the generation of said photons, said imaging device comprising,
- a plurality of detectors arranged around the patient for detecting the spatial distribution of said exiting photons along said detectors,
- at least one of said detectors having a dimension extending perpendicular to said sections and spanning said plurality of sections,
- sectioning means coupled with said detector spanning said plurality of sections to section said detector into a number of sections equal to said plurality of tomographic sections,
- and position circuit means coupled with said spanning detector to establish the position with the detector along said dimension at which said photons are detected.

9. An imaging device as set forth in claim 8, wherein said sectioning means comprises a plurality of spaced apart parallel septa located between said patient and said spanning detector, said plurality of septa being parallel to said sections and forming said tomographic sections between adjacent septum.

10. An imaging device as set forth in claim 8, wherein said sectioning means sections said detector into adjoining sections.

11. An imaging device as set forth in claim 8, wherein said plurality of detectors comprises at least a detector plate and a set of individual elongated side-by-side detectors, said detector plate located opposite said set of elongated detectors on opposite sides of said patient, said detector plate and each of said elongated detectors having a dimension extending perpendicular to and spanning said plurality of tomographic sections, and a plurality of position circuits, with a respective one of said plurality of position circuits being coupled with a respective one of said elongated detectors to determine the position along said spanning dimension at which said photons are detected.

12. An imaging device as set forth in claim 11, wherein said sectioning means comprises a plurality of spaced apart parallel septa located between said patient and said elongated detectors and said patient and said detector plate, said plurality of septa being parallel to said sections and forming said tomographic sections between adjacent septum.

13. An imaging device as set forth in claim 12, further comprising first photomultiplier tube means connected to said detector plate to provide electrical signals when photons are sensed, and second photomultiplier tube means connected to said elongated detectors to provide electrical signals when photons are sensed, and coincidence circuit means connected to said first and second photomultiplier tube means to establish which photons are sensed in the opposite detectors at substantially the same time.

14. An imaging device as set forth in claim 13, wherein the shape of said detector plate is rectangular.

15. An imaging device as set forth in claim 8, wherein each of said plurality of detectors has a dimension extending perpendicular to said sections and spanning said plurality of sections.

16. An imaging device as set forth in claim 15, wherein each of said plurality of detectors is of an elongated shape, with the long dimension of each of said detectors extending perpendicular to said sections and spanning said plurality of sections with each of said plurality of detectors being parallel to each other.

17. An imaging device as set forth in claim 16, wherein said detectors are formed as sets of individual detectors arranged side-by-side, with each set comprising at least two of said detectors.

18. An imaging device as set forth in claim 17, wherein said sets of detectors are located around said patient and are grouped in at least one pair of sets of detectors with each set of said pair being parallel to each other and located on opposite sides of said patient.

19. An imaging device as set forth in claim 18, wherein said plurality of detectors comprises six sets of detectors, with three pairs of opposite sets of detectors being formed.

20. An imaging device as set forth in claim 18, comprising means to rotate said detectors partially around said patient and means to effect a translation motion to each set of said detectors.

21. An imaging device as set forth in claim 15, wherein each of said detectors is of equal length.

22. An imaging device as set forth in claim 17, wherein each of said detectors is connected to a corresponding position circuit means, said sectioning means comprises electronic circuit means connected to said detector and to said position circuit means for establishing said plurality of tomographic sections.

23. An imaging device as set forth in claim 22, wherein each of said detectors comprises a pair of photomultiplier tubes connected to the ends of each of said detectors to detect the exiting photons reacting with the corresponding detector to produce an electrical signal, coincidence circuit means connected to respective photomultiplier tubes of oppositely located detectors to detect exiting photons are sensed in said opposite detector at the same time, said electronic circuit means comprising comparator means connected to respective position circuit means of opposite detectors and to said coincidence circuit means to sense that said simultaneously sensed events occurred at substantially the same locations along the viewing faces of opposite detectors.

24. An imaging device as set forth in claim 22, wherein said sectioning means further comprises a plurlity of sets of spaced apart parallel septa arranged parallel to said section, each of said sets of septa located between said patient and a corresponding set of side-by-side individual detectors.

25. An imaging device as set forth in claim 23, wherein each set of individual detectors comprises at least six elongated detectors, further comprising at least two pairs of said sets of opposite detectors.

26. An imaging device for computerized emission tomography wherein a patient is treated to cause the generation of photons within a three-dimensional region of the patient's body, said photons moving outwardly from within said region and exiting the patient, the region under examination being sectioned into a plurality of aligned parallel planar tomographic sections, said imaging device comprising, a plurlity of detectors located around the patient,
at least one of said detectors having an elongated shape and having its elongated dimension extending perpendicular to the parallel sections and spanning across said plurality of tomographic sections,
and means to simultaneously image said plurality of planar tomographic sections of the region to form a corresponding plurlity of two-dimensional maps of the distribution in the sections of the generation of said photons, for simultaneously generating three dimensional data.

27. An imaging device as set forth in claim 26, wherein said plurality of detectors comprise at least a pair of sets of individual detectors having elongated shapes with the elongated dimensions being parallel, extending perpendicular to and spanning across said plurality of tomographic sections, each set of said pair being located opposite the other set on opposite sides of the patient.

28. An imaging device for computerized emission tomography wherein a patient is treated to cause the generation of photons within a three-dimensional region of the patient's body, said photons moving outwardly from within said region and exiting the patient, n planar tomographic sections of the region being imaged to form two-dimensional maps of the distribution in the section of the generation of said photons, said imaging device comprising, at least one pair of detectors positioned on opposite sides of said patient and having a dimension perpendicular to and spanning said n tomographic sections, and
sectioning means connected to said pair of detectors to section said dectors to form n tomographic sections, where n is an integer greater than 1.

29. In a system for imaging the spatial distribution, in each of a number of substantially parallel and flat slices of a patient, of a radionuclide emitting positrons which cause annihilation events, each generating a pair of annihilation photons propagating along substantially opposite directions from a point within the patient, a detection device comprising:

a first detector system including means for detecting the arrival at a first area of annihilation photons generated by annihilation events occurring in the subject, said first area being disposed on a first side of the subject and being transverse to and spanning said slices;
a second detector system including means for detecting the arrival at a second area of annihilation photons generated by annihilation events occurring in the subject, said second area being disposed on a side of the subject which is opposite said first side and said second area being transverse to and spanning said slices; and
means cooperating with the detector systems for deriving therefrom a number of sets of electrical signals, one set for each of said slices, each set comprising electrical signals each of which defines the orientation within the respective slice of a line statistically likely to be the line of propagation of a pair of annihilation photons generated by a single annihilation event and detected by said detector systems, each set of electrical signals being suitable for processing by a filtered back projection technique to reconstruct an image of the spatial distribution within the respective slice of the annihilation events giving rise to the set of electrical signals, and thereby being suitable for reconstructing an image of the approximate spatial distribution of the radionuclide within the slice.

30. A system as in claim 29 where the deriving means comprise septa which are disposed in planes substantially parallel to the slices and are spaced from each other and are made of a material which substantially absorbs annihilation photons to substantially prevent the concurrent arrival at said first and second areas of annihilation photons propagating along lines which are not within a single one of said slices.

31. A system as in claim 29 where the deriving means comprise:

means for deriving a first detection signal upon the detection of each annihilation photon by the first detector system and a second detection signal upon the detection of each annihilation photon by the second detector system;
means for deriving a coincidence signal upon the concurrent occurrence of a first and a second detection signal;
means for deriving a position signal indicating the slice including the plane in which each annihilation photon is detected by the detector systems;
means for deriving an event signal for each coincidence signal derived for annihilation photons for which position signals have been derived indicating the same slice; and
means for deriving said electrical signals only for said event signals, thereby deriving electrical signals substantially only for annihilation events generating annihilation photons propagating along lines each of which extends within a single one of said slices.

* * * * *

UNITED STATES PATENT AND TRADEMARK OFFICE
CERTIFICATE OF CORRECTION

PATENT NO. : 4,150,292
DATED : April 17, 1979
INVENTOR(S) : Michel M. Ter-Pogossian It is certified that error appears in the above-identified patent and that said Letters Patent are hereby corrected as shown below:

Column 11, line 43, change "and" to --or--.

Column 11, line 64, change "even" to --event--.

Column 12, line 7, change "psoition" to --position--.

Column 13, line 32, change "even" to --event--.

Column 16, line 48, change "tor" to --tors--.

Column 17, line 38, change "dectors" to --detectors--.

Signed and Sealed this

Sixth Day of November 1979

[SEAL]

Attest:

RUTH C. MASON
Attesting Officer

LUTRELLE F. PARKER
Acting Commissioner of Patents and Trademarks